(12) United States Patent
Hibino et al.

(10) Patent No.: US 8,987,533 B2
(45) Date of Patent: Mar. 24, 2015

(54) PRODUCTION METHOD FOR 1-CHLORO-3,3,3-TRIFLUOROPROPENE

(71) Applicant: Central Glass Company, Limited, Ube-shi, Yamaguchi (JP)

(72) Inventors: Yasuo Hibino, Shiki (JP); Satoshi Yoshikawa, Saitama (JP); Fuyuhiko Sakyu, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 14/369,076

(22) PCT Filed: Nov. 22, 2012

(86) PCT No.: PCT/JP2012/080376
§ 371 (c)(1),
(2) Date: Jun. 26, 2014

(87) PCT Pub. No.: WO2013/099485
PCT Pub. Date: Jul. 4, 2013

(65) Prior Publication Data
US 2015/0011806 A1 Jan. 8, 2015

(30) Foreign Application Priority Data
Dec. 29, 2011 (JP) .................. 2011-290306

(51) Int. Cl.
*C07C 17/00* (2006.01)
*C07C 17/278* (2006.01)
*C07C 17/25* (2006.01)

(52) U.S. Cl.
CPC .............. *C07C 17/278* (2013.01); *C07C 17/25* (2013.01); *C07C 2521/04* (2013.01)
USPC ........................................ 570/166; 570/165

(58) Field of Classification Search
USPC ................................................. 570/165, 166
See application file for complete search history.

(56) References Cited

U.S. PATENT DOCUMENTS

| 2,787,646 | A | 4/1957 | Haszeldine |
| 6,018,084 | A | 1/2000 | Nakada et al. |
| 6,235,951 | B1 | 5/2001 | Sakyu et al. |
| 6,844,475 | B1 | 1/2005 | Tung et al. |
| 2003/0028057 | A1 | 2/2003 | Owens et al. |
| 2005/0033097 | A1 | 2/2005 | Tung et al. |
| 2005/0177012 | A1 | 8/2005 | Cohn et al. |
| 2008/0044322 | A1 | 2/2008 | Cohn et al. |
| 2008/0045758 | A1 | 2/2008 | Cohn et al. |

FOREIGN PATENT DOCUMENTS

| EP | 0 939 071 A1 | 9/1999 |
| JP | 1-132782 A | 5/1989 |
| JP | 9-183740 A | 7/1997 |
| JP | 9-194404 A | 7/1997 |
| JP | 10-67693 A | 3/1998 |
| JP | 2000-7592 A | 1/2000 |
| JP | 2001-335517 A | 12/2001 |
| JP | 2003-286209 A | 10/2003 |
| JP | 2007-501843 A | 2/2007 |
| JP | 2008-531474 A | 8/2008 |

OTHER PUBLICATIONS

R. N. Haszeldine, Reactions of Fluorocarbon Radicals. Part V. Alternative Syntheses for Trifluoromethylacetylene (3:3:3-Trifluoropropyne), and the Influence of Polyfluoro-groups on Adjacent Hydrogen and Halogen Atoms, J. Chem. Soc., 1951, p. 2495-2505.
R. N. Haszeldine, Reactions of Fluorocarbon Radicals. Part VII. Addition to Trifluoromethyl-substituted Acetylenes, J. Chem. Soc., 1952, p. 3490-3499.
R. N. Haszeldine, The Addition of Free Radicals to Unsaturated Systems. Part II. Radical Addition to Olefins of the Type R•Ch:Ch$_2$, J. Chem. Soc., 1953, p. 1199-1206.
International Search Report dated Feb. 26, 2013 with English translation (Five (5) pages).
Japanese language Written Opinion (PCT/ISA/237) dated Feb. 26, 2013 (Four (4) pages).

*Primary Examiner* — Jafar Parsa
(74) *Attorney, Agent, or Firm* — Crowell & Moring LLP

(57) ABSTRACT

A production method of 1-chloro-3,3,3-trifluoropropene according to the present invention includes reaction of 1,1,1,3,3-pentachloropropane with hydrogen fluoride, characterized in that the concentrations of respective catalytic components in the 1,1,1,3,3-pentachloropropane as the raw material is controlled to a predetermined level or less. By controlling the concentrations of the respective catalytic components in the 1,1,1,3,3-pentachloropropane to the predetermined level or less, it is possible to improve the problems of shortening of catalyst life, retardation of reaction and scaling or corrosion of equipment in the production of the 1-chloro-3,3,3-trifluoropropene. In addition, the 1,1,1,3,3-pentachloropropane can be obtained selectively with high yield by telomerization reaction of carbon tetrachloride and vinyl chloride. The present invention is thus useful as the method for industrially advantageous, high-yield production of the 1-chloro-3,3,3-trifluoropropene.

10 Claims, No Drawings

PRODUCTION METHOD FOR 1-CHLORO-3,3,3-TRIFLUOROPROPENE

FIELD OF THE INVENTION

The present invention relates to a method for producing 1-chloro-3,3,3-trifluoropropene.

BACKGROUND ART

It is known that 1-chloro-3,3,3-trifluoropropene, that is, the target compound of the present invention can be obtained by various methods such as dehydrochlorination of 3-bromo-3-chloro-1,1,1-trifluoropropane with alcoholic potassium hydroxide (Non-Patent Document 1), addition of hydrogen chloride to 3,3,3-trifluoropropyne (Non-Patent Document 2), dehydroiodination of 3-chloro-1,1,1-trifluoro-3-iodopropane with alcoholic potassium hydroxide (Non-Patent Document 3) or fluorination of 1,3,3,3-tetrachloropropene with hydrogen fluoride in the presence of an antimony catalyst (Patent Document 1).

Further, the present inventors has been disclosed methods of producing 1-chloro-3,3,3-trifluoropropene by fluorination of 1,1,1,3,3-pentachloropropane with hydrogen fluoride in a gas phase in the presence of a solid catalyst or in a liquid phase in the presence of no catalyst (Patent Documents 2, 3 and 4).

PRIOR ART DOCUMENTS

Patent Documents

Patent Document 1: U.S. Pat. No. 2,787,646
Patent Document 2: Japanese Laid-Open Patent Publication No. H09-194404
Patent Document 3: Japanese Laid-Open Patent Publication No. H10-067693
Patent Document 4: Japanese Laid-Open Patent Publication No. 2000-007592 Non-Patent Documents
Non-Patent Document 1: R. N. Haszeldine, J. Chem. Soc., 1951, p. 2495
Non-Patent Document 2: J. Chem. Soc., 1952, p. 3490
Non-Patent Document 3: J. Chem. Soc., 1953, p. 1199

SUMMARY OF THE INVENTION

Problems to be Solved by the Invention

The methods of Non-Patent Documents 1 and 3, each of which involves dehydrohalogenation with potassium hydroxide, show high conversion rate and high selectivity but have difficulties in industrial applications due to the need to use more than the stoichiometric amount of potassium hydroxide and the need to prepare 3-bromo-3-chloro-1,1,1-trifluoropropane or 3-chloro-1,1,1-trifluoro-3-iodopropane in advance as the raw material. The method of Non-Patent Document 2, which involves addition of hydrogen chloride, shows high reaction rate and high selectivity but faces the problem that it is difficult to obtain 3,3,3-trifluoropropyne as the raw material. The method of Patent Document 1, which involves fluorination with hydrogen fluoride in the presence of an antimony catalyst, faces the problems that it is difficult to obtain the raw material and to perform the reaction in a quantitative manner.

On the other hand, it is considered that the production of 1-chloro-3,3,3-trifluoropropene by fluorination of relatively readily available 1,1,1,3,3-pentafluoropropane with hydrogen fluoride is suitable for industrial production purposes.

In general, the production method of 1-chloro-3,3,3-trifluoropropene, that is, the target compound of the present invention includes a first step of forming 1,1,1,3,3-pentachloropropane by reaction of carbon tetrachloride and vinyl chloride and a second step of forming 1-chloro-3,3,3-trifluoropropene by fluorination of the 1,1,1,3,3-pentachloropropane obtained in the first step and separating and purifying the thus-formed 1-chloro-3,3,3-trifluoropropene as shown in the following scheme. In the first step, the reaction is commonly performed in the presence of a catalyst. This leads to the existence of impurities, such as components of the catalyst, in the 1,1,1,3,3-pentachloropropane and raises the problems of shortening of catalyst life, retardation of reaction, serious corrosion of reaction equipment etc.

[First Step] Formation of 1,1,1,3,3-pentachloropropane (addition reaction)

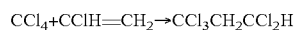

[Second Step] Formation of 1-chloro-3,3,3-trifluoropropene (fluorination reaction)

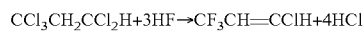

It is accordingly an object of the present invention to provide a method for efficiently producing 1-chloro-3,3,3-trifluoropropene on an industrial scale by fluorination of 1,1,1,3,3-pentachloropropane with hydrogen fluoride without causing load on reaction equipment.

Means for Solving the Problems

In view of the above prior art problems, the present inventors have made extensive researches on various production techniques in order to establish a suitable method for industrial-scale production of 1-chloro-3,3,3-trifluoropropene. As a result of the researches, the present inventors have found that, in the case of producing 1-chloro-3,3,3-trifluoropropene from 1,1,1,3,3-pentachloropropane, it is possible to remedy the problems of shortening of catalyst life, retardation of reaction, scaling or corrosion of reaction equipment etc. by controlling the concentrations of respective catalytic components (such as metal solubilizer and its hydrochloride salt etc.) in the 1,1,1,3,3-pentachloropropane to a predetermined level or less. The present inventors have also made researches the telomerization reaction of carbon tetrachloride and vinyl chloride in the presence of a catalyst for the preparation of the 1,1,1,3,3-pentachloropropane as the raw material and found that it is possible to obtain the target 1,1,1,3,3-pentachloropropane selectively with high yield by the use of a catalyst containing elemental iron as a main component in combination of a specific metal solubilizer.

Namely, the present invention includes the following Inventive Aspects 1 to 10.

[Inventive Aspect 1]

A method for producing 1-chloro-3,3,3-trifluoropropene, comprising reacting 1,1,1,3,3-pentachloropropane with hydrogen fluoride in a reaction system, wherein the method comprises a concentration control step of controlling the concentrations of a metal solubilizer and/or a hydrochloride salt thereof and an iron complex in the 1,1,1,3,3-pentachloropropane supplied to the reaction system to be 100 ppm or less.

[Inventive Aspect 2]

The method according to Inventive Aspect 1, wherein the metal solubilizer is at least one kind selected from the group consisting of N,N-dimethylacetamide, acetonitrile, 2-aminoacetonitrile, N,N-dimethylformamide and hexamethylphosphoric amide.

[Inventive Aspect 3]

The method according to Inventive Aspect 1, wherein the iron complex is a complex of N,N-dimethylacetamide, iron (II) chloride and iron (III) chloride ($FeCl_2 \cdot 2FeCl_3 \cdot 6DMAC$).

[Inventive Aspect 4]

The method according to any one of Inventive Aspects 1 to 3, wherein the concentration control step includes, before supplying the 1,1,1,3,3-pentachloropropane to the reaction system, removing the metal solubilizer and/or the hydrochloride salt thereof and the iron complex from the 1,1,1,3,3-pentachloropropane by adsorption onto an adsorbent.

[Inventive Aspect 5]

The method according to any one of Inventive Aspects 1 to 3, wherein the concentration control step includes, before supplying the 1,1,1,3,3-pentachloropropane to the reaction system, removing the metal solubilizer and/or the hydrochloride salt thereof and the iron complex from the 1,1,1,3,3-pentachloropropane by washing with water.

[Inventive Aspect 6]

The method according to any one of Inventive Aspects 1 to 5, further comprising: forming the 1,1,1,3,3-pentachloropropane by reaction of carbon tetrachloride and vinyl chloride in the presence of an iron catalyst.

[Inventive Aspect 7]

The method according to Inventive Aspect 6, wherein the concentration of the iron catalyst used in the reaction of the carbon tetrachloride and the vinyl chloride is 100 ppm or less in terms of iron.

[Inventive Aspect 8]

The method according to any one of Inventive Aspects 1 to 5, wherein the 1,1,1,3,3-pentachloropropane is reacted with the hydrogen fluoride in the absence of a catalyst in a temperature range of 100 to 500° C. and in a pressure range of 0.05 to 6.0 MPa.

[Inventive Aspect 9]

The method according to any one of Inventive Aspects 1 to 5, wherein the 1,1,1,3,3-pentachloropropane is reacted with the hydrogen fluoride in a gas phase in the presence of a fluorination catalyst.

[Inventive Aspect 10]

The method according to Inventive Aspect 9, wherein the fluorination catalyst is at least one kind selected from the group consisting of fluorinated stainless steel, fluorinated alumina, fluorinated zirconia, fluorinated titania, activated carbon, chromium-carried alumina and chromium-carried activated carbon.

In the production method of the present invention, it is possible to prevent corrosion of equipment and degradation of catalyst by controlling the concentrations of the respective contaminant impurities in the raw material 1,1,1,3,3-pentachloropropane. The production method of the present invention is useful for high-yield industrial production of the target 1-chloro-3,3,3-trifluoropropene.

DESCRIPTION OF THE EMBODIMENTS

Hereinafter, the present invention will be described below in detail. It should be noted that: the scope of the present invention is not limited to the following description; and various changes and modifications can be made as appropriate without impairing the scope of the present invention. All of the publications cited in the present specification, such as prior art documents and patent documents e.g. published patents and patent applications, are herein incorporated by reference.

The production method of the present invention can be carried out through the following steps: a first reaction step of forming 1,1,1,3,3-pentachloropropane as the raw material; a concentration control step of controlling the concentrations of respective contaminant impurities in the 1,1,1,3,3-pentachloropropane obtained in the first reaction step; and a second reaction step of forming 1-chloro-3,3,3-trifluoropropene by reacting, with hydrogen fluoride, the 1,1,1,3,3-pentachloropropane obtained after the concentration control step.

First, the first reaction step will be explained below. In the first reaction step, the 1,1,1,3,3-pentachloropropane can be formed by telomerization reaction of carbon tetrachloride and vinyl chloride in the presence of an iron catalyst.

The iron catalyst used in the first reaction step is a catalyst containing iron. There can be used metal iron, pure iron, soft iron, steel containing carbon or alloy containing iron as a component. For example, various kinds of stainless steels and ferrosilicons are useable. Further, the iron catalyst can be used in any form such as powder, particles, block, wire, rod, sphere, plate, arbitrary-shaped metal piece obtained therefrom, e.g., distillation packing like Raschig ring or Helix, indefinite-shaped metal piece e.g. steel wool, mesh or coil, or the like. It is not preferable to use the alloy containing not only iron but also a large amount of catalytically inactive components because the catalytically inactive components are eluted or present as an insoluble matter in the reaction system and are difficult to process after the reaction.

As the main component of the catalyst, it is necessary to use the iron in an amount of at least 0.001 mol per 1 mol of the carbon tetrachloride. In a batch reaction process or semi-batch reaction process, the amount of the iron used is generally 0.001 to 1 mol, preferably 0.005 to 0.8 mol, more preferably 0.01 to 0.5 mol, per 1 mol of the carbon tetrachloride. In a flow reaction process, there would be no particular problem even when the iron is used in an excessive amount of more than 1 mol. It is however not favorable set the amount of the iron to be less than 0.001 mol in view of deterioration of reaction yield.

A metal compound or metal complex having the function of a promotor can be used in combination with the iron. As a metal of such a metal compound or metal complex, metals of Group VII or Group IB of the periodic table are suitably usable. More specifically, there can be used a halide, oxide, nitrate, acetate or acetylacetone complex of nickel, iron, cobalt, palladium, ruthenium, copper or silver as the promotor. It is particularly preferable to use a halide of metal selected from nickel, iron, cobalt and copper. The halide can be either a fluoride, chloride, bromide, iodide or the like. Among others, chloride is preferred in view of reactivity, versatility and ease of handling. Preferred examples of the chloride are ferrous chloride, ferric chloride, nickel chloride, cobalt chloride, cuprous chloride and cupric chloride.

The amount of the promoter used is generally 0.001 to 1 mol, preferably 0.05 to 0.5 mol, more preferably 0.01 to 0.1 mol, per 1 mol of the carbon tetrachloride. It is not favorable to set the amount of the promoter to be less than 0.001 mol in view of deterioration of reaction rate. The ratio of the amount of the promoter used relative to the iron is not particularly limited because the amount of the iron is not particularly limited as mentioned above. In general, the ratio of the amount of the promoter used relative to the iron is preferably 0.1 or less.

In the first reaction step, the metal component is solubilized at a given temperature or higher in the coexistence of an organic halogen compound such as carbon tetrachloride and a metal solubilizer. Namely, the target 1,1,1,3,3-pentachloropropane can be selectively formed with high yield by the combined use of the iron catalyst and the metal solubilizer.

As the metal solubilizer, there can suitably be used an aprotic polar organic compound such as nitrile, amide, phosphite or other. Specific examples of the nitrile are acetonitrile, propionitrile, butyronitrile, valeronitrile, benzonitrile, isophthalonitrile, 2-pentenenitrile and 3-pentenenitrile. Specific examples of the amide are dimethylformamide, dimethylacetamide and hexamethylphosphoric amide. Specific examples of the phosphite are trimethyl phosphite, triethyl phosphite, tripropyl phosphite and tributyl phosphite. Specific examples of the other aprotic polar organic compound are dimethyl sulfoxide, N-methyl-2-pyrrolidone, 1,3-dimethyl-2-imidazolidinone and γ-butyrolactone. Among others, acetonitrile, 2-aminoacetonitrile, N,N-dimethylformamide, dimethylformamide and hexamethylphosphoric amide are preferred in view of high solubility of the metal compound. The above metal solubilizer compounds can be used solely or in the form of a mixture of two or more thereof.

For improvements in reactivity and selectivity, an inert solvent may be added to the reaction system as appropriate. In general, the addition of such a solvent is effective in reducing the generation of a high polymer of vinyl chloride. The amount of the solvent added is not particularly limited and can be adjusted as appropriate. The kind of the solvent added is not also particularly limited as long as the solvent is inert and does not function as a radial scavenger in the reaction system.

The molar ratio of the metal solubilizer/the carbon tetrachloride in the reaction system is generally 10/1 to 1/1000, preferably 1/10 to 5/1000, particularly preferably about 1/100. There would be no particular problem even when the molar ratio is larger than 10/1. It is however not favorable to set the molar ratio to such a large value in view of upsizing of the reactor. It is also not favorable to set the molar ratio to be smaller than 1/1000 in view of deterioration of reactivity between the carbon tetrachloride and the vinyl chloride.

It is preferable to use the vinyl chloride in an equimolar amount or less relative to the carbon tetrachloride. The amount of the vinyl chloride used is not however limited to the equimolar amount. When the amount of the vinyl chloride is more than equimolar, there may be caused unfavorable results such as increases in the amount of the high vinyl chloride polymer generated in the reaction system and in the amount of the vinyl chloride remaining unreacted and passing through the reactor. The amount of the vinyl chloride is thus preferably equimolar or less to the carbon tetrachloride in order to decrease the generation of the high polymer. It is particularly preferable that the amount of the vinyl chloride is about 1/2 of the amount of the carbon tetrachloride. When the amount of the vinyl chloride is equimolar or less to the carbon tetrachloride, some of the carbon tetrachloride remains unreacted in the reaction system. There would however be no problem because the unreacted carbon tetrachloride can be recovered from the reaction solution by any known process such as distillation and then recycled.

It is feasible in the first reaction step to use the vinyl chloride by dilution with an inert gas. The degree of dilution of the vinyl chloride can be set arbitrarily. Not only the amount of the high vinyl chloride polymer generated but also the efficiency of equipment decrease with increase in the proportion of the diluent gas to the vinyl chloride. Thus, the volume ratio of the vinyl chloride/the dilute gas is generally of the order of 0.1 to 10. The kind of the diluent gas is particularly limited as long as the diluent gas is inert and does not function as a radial scavenger in the reaction system. For example, there can be used nitrogen, hydrogen, argon, helium or the like as the diluent gas.

The temperature of the reaction varies depending on the amounts of the iron, the promoter and the metal solubilizer used and exerts an influence on the conversion rate of the vinyl chloride, the selectivity of the 1,1,1,3,3-pentachloropropane, the life of the catalyst and the life of the promoter. In the first reaction step, the reaction temperature is generally 80 to 150° C., more preferably 100 to 120° C. The conversion rate of the vinyl chloride is unfavorably deteriorated when the reaction temperature is lower than 80° C. When the reaction temperature is higher than 150° C., it is unfavorably necessary to increase the pressure of the reactor. The pressure of the reactor is the sum of the partial pressure of the carbon tetrachloride and the partial pressure of the metal solubilizer at each temperature. The pressure of the reactor is generally 1 to 50 kg/cm$^3$, preferably 3 to 15 kg/cm$^3$.

In the first reaction step, any of batch reaction process, semi-batch reaction process and flow reaction process can be adopted. For example, it is preferable to perform the reaction by adding the iron and optionally the metal compound and/or metal complex (as catalytic components) in a mixed solution of the carbon tetrachloride and the metal solubilizer, and then, continuously or intermittently introducing the vinyl chloride in gas form or liquid form to the resulting mixed solution. It is preferable to avoid feeding the iron, the metal solubilizer and the reagents in advance in the batch reactor and to avoid sequentially adding the vinyl chloride in liquid form because those reaction processes tend to increase the generation of the high vinyl chloride polymer. In the case where the iron is relatively small in size and shape, the iron may be floated or flowed in the reaction system by stirring with the reaction solution. Alternatively, the iron may be fixed while allowing the flow of the other reagents. In any reaction process, gas-liquid contact is an important factor to the reaction. It is thus preferable to use any known instrument or device for gas-liquid contact in the reaction system. For example, various known devices for gas-liquid contact, such as stirrer and sparger, are usable.

One example of the first reaction step is to introduce reduced iron (Fe) and N,N-dimethylacetamide (DMAC) as the catalytic components continuously together with the raw materials, i.e., vinyl chloride and carbon tetrachloride into the corrosion-resistant glass-lined reactor under the conditions of 130 to 140° C. and 0.3 MPa. In this case, a flowable liquid iron complex, i.e., a "complex of N,N-dimethylacetamide, iron (II) chloride and iron (III) chloride ($FeCl_2.2FeCl_3.6DMAC$)" (sometimes simply referred to as "iron complex" in the present specification) is formed by the N,N-dimethylacetamide and iron (II) and (III) chlorides generated from the reduced iron and the chloride compound, and then, involved in the reaction. The resulting catalyst composition is continuously discharged together with the 1,1,1,3,3-pentachloropropane, carbon tetrachloride, DMAC and its hydrochloride salt as the reaction mixture from the reaction system. The reaction mixture is, when cooled and left still, separated into two layers: a flowable liquid catalyst layer and an organic crude product layer. However, each of the iron complex and DMAC (and its hydrochloride salt) has solubility in the organic crude product layer. Consequently, the iron complex and DMAC (and its hydrochloride salt) are dissolved and present in slight amounts in the organic crude product layer.

The present inventors have found that, by controlling each of the concentrations of the above contaminant impurities such as iron complex to a predetermined level or less, it is possible to avoid the problems of equipment corrosion in the first reaction step as well as catalyst life shortening, reaction retardation, equipment corrosion etc. in the subsequent second reaction step. In other words, it is possible to efficiently conduct the second reaction step, without causing an adverse influence such as corrosion on equipment e.g. reservoir or distillation column, when the concentrations of the iron complex and the metal solubilizer and/or hydrochloride salt thereof in the 1,1,1,3,3-pentachloropropane obtained in the first reaction step are each controlled to 100 ppm or less, preferably 10 ppm or less, by the concentration control step.

Specific embodiments of the concentration control step will be explained below in detail.

In general, 1,1,1,3,3-pentachloropropane (boiling point: 179° C.) can be isolated and purified by vacuum distillation of a crude product thereof. In the case where the impurities such as iron complex and DMAC and/or its hydrochloride salt or metal solubilizer close in boiling point are present in the 1,1,1,3,3-pentachloropropane, the vacuum distillation of the 1,1,1,3,3-pentachloropropane causes an unfavorable result such as partial decomposition of the iron complex whereby the resulting DMAC hydrochloride salt undergoes sublimation or entrainment distillation and causes clogging or corrosion of the upper part of the distillation column. Further, the metal solubilizer (or its salt) mixed in the purified 1,1,1,3,3-pentachloropropane unfavorably becomes a cause of shortening of catalyst life, retardation of reaction or scaling or corrosion of equipment in the subsequent step.

Although the occurrence of equipment corrosion etc. can be retarded by the addition of a glycidyl ether stabilizer as an acid scavenger, the effect of such a stabilizer is limited. It is thus preferable to first control the concentrations of the respective contaminant impurities such as catalyst components to the predetermined level or less and then add the stabilizer as needed.

It is feasible to separate and remove the contaminant impurities by adsorption on an adsorbent, washing with water, membrane separation, distillation etc. Activated alumina, zeolite, silica gel, activated carbon, cellulose fiber etc. are usable as the adsorbent. The impurities can be removed by continuously introducing the organic substance into a column packed with the adsorbent or bringing a predetermined amount of the organic substance into contact with the adsorbent in a batch manner. The adsorbent can be recycled after eliminating the adsorbed components from the adsorbent by treatment with an organic solvent such as acetone, methanol or ethyl acetate, water vapor etc. and drying the adsorbent. For reduction of the adsorbent, it is a preferred embodiment to perform distillation after the adsorption on the adsorbent. There is no particular limitation on the technique of the distillation. The distillation technique can be selected as appropriate by any skilled in the art.

In the case of washing the impurities away with water, the amount of the water used relative to the organic substance containing the iron complex varies depending on the concentrations of the respective impurities such as iron complex and metal solubilizer. When the organic substance contains 0.1 mass % of the iron complex and 0.05 mass % of the metal solubilizer, for example, it suffices that the amount of the water used relative to the organic substance is in a range of 1/1 to 1/4. Although the water can be used in an amount of 1/1 or more, the use of a larger amount of water is disadvantageous in operation and economical. The effect of the water washing is poor when the amount of the water used is less than 1/4. When the effect of the water washing is not sufficient due to the high concentrations of the impurities, it is preferable to repeat the water washing a plurality of times. The temperature of the water can be any temperature as long as the water can be used in liquid form with no problem in operation. In general, the temperature of the water is preferably 20 to 80° C. After the water washing, the organic substance is subjected to two-layer separation and dried by contact with a drying agent such as zeolite.

As explained above, the contaminant impurities such as iron complex, DMAC and its hydrochloride salt or metal solubilizer contained in the 1,1,1,3,3-pentachloropropane can be reduced by various purification processes.

Next, the second reaction step will be explained. In the second reaction step, the 1,1,1,3,3-pentachloropropane can be reacted with hydrogen fluoride in a gas phase in the presence of a fluorination catalyst, or under high-temperature and high-pressure conditions in the presence of no catalyst.

In the second reaction step, the corrosive hydrogen fluoride is used under high-temperature conditions. Although stainless steel etc. having resistance to corrosion by hydrogen fluoride or hydrogen chloride is preferred, it is necessary to retard the corrosion-promoting material. The problems of catalyst life shortening, reaction retardation and equipment corrosion can be avoided when the concentration of the metal solubilizer is 100 ppm or less, preferably 10 ppm or less, as mentioned above.

In the case where the reaction is performed in a gas phase in the presence of the fluorination catalyst, there can be used a metal compound-carried catalyst as the fluorination catalyst. Further, a fluorination product of alumina, titania, stainless steel or the like (e.g. fluorinated alumina) or an activated carbon is suitably usable as the fluorination catalyst. Although the alumina can be in various forms depending on its preparation process, there is no particular limitation on the form of the alumina used in the present invention. In general, γ-alumina is readily available and suitable for use. Among others, preferred is activated alumina having a relatively large specific surface and high heat resistance for use as a catalyst carrier. The stainless steel can be either ferrite stainless steel SUS 430 or austenite stainless steel SUS 304, 304L, 315 or 316L. In view of increase of surface area, the stainless steel is preferably used in the form of stainless wool, stainless mesh, fine wire, fine tube or arbitrary-shaped distillation packing obtained therefrom.

A metal-carried catalyst in which a metal is carried on a carrier is also suitably usable as the fluorination catalyst. In this case, the metal is selected from metals of Group 4, Group 5, Group 6, Group 7, Group 8, Group 9, Group 10, Group 11, Group 13, Group 14 and Group 15 of the periodic table. As the metal-carried catalyst, preferred are those in which an oxide, fluoride, chloride, fluorochloride, oxyfluoride, oxychloride or oxyfluorochloride of one kind of metal or two or more kinds of metals selected from chromium, titanium, aluminum, manganese, nickel, cobalt and zirconium is carried on activated carbon. Alumina, fluorinated alumina, fluorinated aluminum, zirconia or fluorinated zirconia can alternatively be used as the carrier.

There is no particular limitation on the preparation process of the metal-carried catalyst. It is feasible to prepare the metal-carried catalyst by e.g. providing a solution dissolving therein a soluble compound of one kind of metal or two or more kinds of metals selected from chromium, titanium, manganese, nickel and cobalt and activated carbon as it is or in halogen-modified form by treatment with hydrogen fluoride, hydrogen chloride, chlorofluorohydrocarbon etc., and then, impregnating the activated carbon with the solution or spraying the solution onto the activated carbon.

Examples of the activated carbon usable as the catalyst or carrier are: plant-based activated carbons prepared using wood, wood charcoal, coconut shell charcoal, palm shell charcoal, raw ash etc. as raw materials; coal-based activated carbons prepared using peat coal, lignite, brown coal, bituminous coal, anthracite etc. as raw materials; petroleum-based activated carbons prepared using petroleum pitch, oil carbon etc. as raw materials; and synthetic resin-based activated carbons prepared using polyvinylidene chloride etc. as raw materials. These activated carbons are commercially available and usable. For example, there can be used bituminous coal activated carbon (granular activated carbon available under the trade name of BPL from Toyo Calgon Co., Ltd.), coconut shell activated carbon (available under the trade name of Granular Shirasagi GX, G2X, SX, CX or XRC from Japan EnviroChemicals Ltd. or available under the trade name of PCB from Toyo Calgon Co., Ltd.). The activated carbon is not however limited to the above examples. In general, the activated carbon is used in the form of particles. The shape and size of the activated carbon can be selected as appropriate based on the general knowledge of those skilled in the art as long as the activated carbon is adaptable to the reactor. The activated carbon can be in various forms such as spherical form, fibrous form, powder form and honeycomb form. The specific surface and pore volume of the activated carbon can be within the specifications of commercially available activated carbons. It is preferable that the activated carbon has a specific surface of larger than 400 $m^2/g$ and a pore volume of larger than 0.1 $cm^3/g$. The activated carbon may preferably have a specific surface of 800 to 3000 $m^2/g$ and a pore volume of 0.2 to 1.0 $cm^3/g$. It is further preferable, in the case of using the activated carbon as the carrier, to activate a surface of the carrier and remove an ash content from the surface of the carrier by immersing the carrier in an aqueous basic solution of ammonium hydroxide, sodium hydroxide, potassium hydroxide etc. for about 10 hours or more at around room temperature or by pretreating the carrier with an acid such as nitric acid, hydrochloric acid or hydrofluoric acid as is commonly done.

The amount of the metal carried is generally 0.1 to 80 wt %, preferably 1 to 40 wt %. The soluble compound of the metal carried on the activated carbon can be either a nitrate, a chloride, an oxychloride or an oxide of the metal, which is soluble in a solvent of water, methanol, ethanol, acetone or the like. Specific examples of the soluble metal compound are chromium nitrate, chromium trichloride, chromium trioxide, potassium dichromate, titanium trichloride, manganese nitrate, manganese chloride, manganese dioxide, nickel nitrate, nickel chloride, cobalt nitrate and cobalt chloride.

Regardless of how the metal-carried catalyst is prepared, it is effective to treat the catalyst with a fluorination agent such as hydrogen fluoride or fluorinated (and chlorinated) hydrocarbon at a temperature higher than a predetermined reaction temperature in advance of use for the purpose of preventing the composition of the catalyst from changing during the reaction. It is also effective to feed oxygen, chlorine, fluorinated or chlorinated hydrocarbon or the like into the reactor during the reaction for improvements in catalyst life, reaction rate and reaction yield.

In the second reaction step, the contact time of the reaction is generally 0.1 to 300 seconds, preferably 1 to 50 seconds, in view of productivity.

The temperature of the reaction is generally 100 to 500° C. in the second reaction step. In the liquid-phase reaction, the reaction temperature is preferably 100 to 200° C. The reaction temperature is preferably 150 to 350° C. in the gas-phase reaction. The rate of the reaction is low when the reaction temperature is lower than 100° C.

The pressure of the reaction is generally 0.05 to 6.0 MPa in the second reaction step. In the liquid-phase reaction, the preferable range of the reaction pressure is 0.5 to 6.0 MPa because it is desired that the organic raw material, intermediate and hydrogen fluoride are liquefied in the reaction system. In the gas-phase reaction, the preferable range of the reaction pressure is 0.05 to 5.0 MPa, practically about 0.05 to 1.0 MPa.

A continuous reaction process, which allows continuous introduction of the raw material to the reaction system and continuous discharge of the product compound, is suitably adopted for the gas-phase reaction. For the liquid-phase reaction, either a batch reaction process in which the raw material is maintained in the reactor for a predetermined time but also a continuous reaction process in which the raw material is continuously introduced while the product compound is recovered by distillation separation (reaction distillation) of the by-produced hydrogen chloride and organic substance and unreacted hydrogen fluoride with the use of a reflex condenser on the upper part of the reactor can be adopted.

In the gas-phase reaction, it is effective regardless of how the metal-carried catalyst is prepared to treat the catalyst with a fluorination agent such as hydrogen fluoride or fluorinated (and chlorinated) hydrocarbon at a temperature higher than a predetermined reaction temperature in advance of use for the purpose of preventing the composition of the catalyst from changing during the reaction. It is also effective to feed oxygen, chlorine, fluorinated or chlorinated hydrocarbon or the like into the reactor during the reaction for improvements in catalyst life, reaction rate and reaction yield.

The molar ratio of the 1,1,1,3,3-pentachloropropane/the hydrogen fluoride supplied to the reaction system varies depending on the reaction temperature. In the gas-phase reaction, the molar ratio of the 1,1,1,3,3-pentachloropropane/the hydrogen fluoride is generally 1/3 to 1/20, preferably 1/3 to 1/10. When the amount of the hydrogen fluoride is too large, the reactor is uneconomically increased in size. When the amount of the hydrogen amount is too small, the organic substance is likely to undergo polymerization so that the yield of the target product compound decreases with decrease in reactivity. In the liquid-phase reaction, it is preferable to use the hydrogen fluoride in an excessive amount of at least 10 equivalents or more, more preferably 20 equivalents or more, still more preferably 40 equivalents or more, relative to the 1,1,1,3,3-pentachloropropane. Although the target product compound is generally entrained with lower fluorination products and unreacted reactant and hydrogen fluoride, these entrained substances can be separated from the target product compound and recycled. The use of such an excessive or less amount of hydrogen fluoride is not critical in large-scale production.

The reactor is preferably formed of a material having not only heat resistance but also resistance to corrosion by hydrogen fluoride or hydrogen chloride etc. Among others, stainless steel, Hastelloy alloy or Monel alloy is preferred as the material of the reactor. The reactor may alternatively be formed of a material having a lining of the above metal.

The thus-obtained reaction product containing the 1-chloro-3,3,3-trifluoropropene and discharged out of the reactor is purified to a final product by any known process. There is no particular limitation on the purification process. For example, the reaction product can be purified by washing the reaction product with water and/or aqueous solution to remove acid component such as hydrogen chloride and hydrogen fluoride from the reaction product, drying the washed reaction product, and then, subjecting the dried reaction product to distillation to remove organic impurity component from the dried reaction product.

EXAMPLES

The present invention will be described in more detail below by way of the following examples. In the following examples, all percentages (%) of gas chromatographic analysis values are mass %. Further, the term "iron complex" refers to "FeCl$_2$.2FeCl$_3$.6DMAC" in the following working examples, reference examples and comparative examples.

Preparation Example 1

First, 300 g of activated alumina (NKH3-24 available from Sumitomo Chemical Co., Ltd., particle size: 2 to 4 mm, specific surface: 340 m$^2$/g) was weighed out. A powdery substance adhered to a surface of the activated alumina was removed by washing with water. Further, 10% aqueous hydrogen fluoride solution was prepared by dissolving 115 g of hydrogen fluoride (anhydrous hydrofluoric acid) in 1035 g of water. The washed activated alumina was gradually dropped into the prepared 10% aqueous hydrogen fluoride solution. The resulting mixture was stirred for 3 hours, left still and washed with water. The resulting activated alumina was filtered out and dried for 2 hours at 200° C. by an electric furnace. After that, 150 cc of the dried activated alumina was placed in a stainless reaction tube of 1 inch inner diameter and 30 cm length. While flowing nitrogen through the reaction tube, the reaction tube was heated to 200° C. by an electric furnace. Hydrogen fluoride was introduced together with the nitrogen into the reaction tube so that the activated alumina was treated with the hydrogen fluoride. Although the temperature of the reaction tube was raised with the progress of the treatment, the flow rate of the nitrogen and the hydrogen fluoride was adjusted in such a manner that the temperature of the reaction tube did not exceed 400° C. After the heat generation was settled, the electric furnace was maintained at 400° C. for 2 hours. The preparation of the catalyst was then completed.

Example 1

Production of 1,1,1,3,3-pentachloropropane

Into a 1000-ml glass autoclave reactor with a stirrer, 3.2 mol of carbon tetrachloride, 0.8 mol of chloroform, 0.06 mol of N,N-dimethylacetamide (DMAC) (1.25 mol % relative to the carbon tetrachloride) and 0.02 mol of iron powder (0.625 mol % relative to the carbon tetrachloride) were fed. The reactor was sealed after the air inside the reactor was replaced with nitrogen gas. Then, the content of the reactor was heated to 140° C. and maintained for 30 minutes while stirring at 250 rpm. At this time, the pressure of the reactor was 0.25 MPaG (gauge pressure; hereinafter, the same applies to the following). After the lapse of 30 minutes, vinyl chloride was injected into the reactor so that the pressure of the reactor became approximately 0.33 MPaG. With the progress of the reaction, vinyl chloride was further injected into the reactor so as to maintain the pressure of the reactor. The total amount of the vinyl chloride injected was 2 mol. The reaction time was 160 minutes.

After the completion of the reaction, the reactor was cooled naturally. The content was taken out of the reactor. A metal salt was removed from the reactor content. The reactor content was subsequently analyzed by gas chromatograph.

The yield of the target 1,1,1,3,3-pentachloropropane relative to the amount of the carbon tetrachloride fed was 55.1 mol %. The amount of the carbon tetrachloride remaining unreacted was 1.35 mol (42.2% relative to the amount of the carbon tetrachloride fed). The reaction rate of the vinyl chloride and the selectivity of the 1,1,1,3,3-pentachloropropane were 97.6% and 92.7%, respectively.

Example 2

Production of 1,1,1,3,3-pentachloropropane

The reaction, recovery and analysis was carried out in the same manner as in Example 1, except for using 0.06 mol of hexamethylphosphoric amide in place of DMAC. The reaction time was 180 minutes. The yield of the target 1,1,1,3,3-pentachloropropane relative to the amount of the carbon tetrachloride fed was 54.4 mol %. The amount of the carbon tetrachloride remaining unreacted was 1.22 mol (38.1% relative to the amount of the carbon tetrachloride fed). The reaction rate of the vinyl chloride and the selectivity of the 1,1,1,3,3-pentachloropropane were 96.8% and 93.1%, respectively.

Reference Example 1

In a 100-ml container of SUS 304 (Ni: 8 to 10.5%, Cr: 18 to 20%), a test piece of SUS 317L (Ni: 11 to 15%, Cr: 18 to 20%, Mo: 3 to 4%; ultralow-carbon steel), 10 g of 1,1,1,3,3-pentachloropropane and a predetermined amount of iron complex were sealed. After that, the container was degassed and then heated at 150° C. for 24 hours. The corrosion rate and the scaling rate (the rate of increase of solid matter adhered per unit area) of the test piece was determined by measuring the weight of the test piece before and after the above test operation. The determination results are shown in TABLE 1.

TABLE 1

| Test No. | Additive | Fe concentration ppm | Corrosion rate mm/y | Scaling rate g/m$^2$ · day |
|---|---|---|---|---|
| 1 | none | 0 | 0.000 | 0.95 |
| 2 | Fe complex | 5300 | 1.057 | 209.15 |
| 3 | Fe complex | 570 | 0.094 | 20.49 |
| 4 | Fe complex | 94 | 0.019 | 1.74 |

Fe complex: FeCl$_2$ · 2FeCl$_3$ · 6DMAC
Judgment of corrosion rate (erosion degree)
fully resistant to corrosion: ≤0.05 mm/y
quite resistant to corrosion: 0.05 to 0.10 mm/y
rather resistant to corrosion: 0.1 to 0.5 mm/y
slightly resistant to corrosion: 0.5 to 1.0 mm/y
not resistant to corrosion: ≥1.0 mm/y As is apparent from the above results, there occurred less corrosion and scaling of SUS 317L when the concentration of the iron complex was 94 ppm in terms of iron.

Example 3

Production of 1-chloro-3,3,3-trifluoropropene

In a 300-ml SUS 316 autoclave reactor with a stirrer, a test piece of SUS 317L was placed. After the reactor was cooled and degassed, 50 g (0.23 mol) of 1,1,1,3,3-pentachloropropane, 100 g (5 mol) of anhydrous hydrofluoric acid and a predetermined amount of N,N-dimethylacetamide (DMAC) were fed into the reactor. The content of the reactor was heated at 160° C. while stirring at 250 rpm.

After the pressure of the reactor reached 4.2 MPaG, the content of the reactor was maintained for 5 hours. The reactor was cooled with ice after the completion of the reaction. The test piece and organic substance were taken out of the reactor. The organic substance was analyzed by gas chromatograph.

It was confirmed by analysis of the organic substance that: the conversion rate of the 1,1,1,3,3-pentachloropropane was 99.9% or more; and the selectivity of the target 1-chloro-3,3,3-trifluoropropene was 90 to 95% (trans/cis isomer ratio: about 10/1).

The corrosion rate and the scaling rate (the rate of increase of solid matter adhered per unit area) of the test piece was determined by measuring the weight of the test piece before and after the above test operation. The determination results are shown in

TABLE 2

| Test No. | Additive | Fe concentration ppm | Corrosion rate mm/y | Scaling rate g/m$^2$ · day |
|---|---|---|---|---|
| 1 | none | 0 | 0.000 | 0.38 |
| 2 | DMAC | 100 | 0.000 | 0.76 |
| 3 | DMAC | 250 | 0.018 | 1.52 |
| 4 | DMAC hydrochloride salt | 1140 | 0.054 | 7.22 |

As mentioned above, the reaction was performed with the use of an excessive amount of hydrogen fluoride under high-temperature and high-pressure conditions. It has been shown by the above results that it is preferable to set the amount of the DMAC to be 100 ppm or less for minimization of scaling and corrosion.

Reference Example 2

In a 100-ml glass bottle with a screw cap, a predetermined amount of N,N-dimethylacetamide (DMAC) and an adsorbent were sealed and left for 30 minutes at room temperature. After that, the organic substance was analyzed by gas chromatograph. The analysis results are shown in TABLE 3.

TABLE 3

| Test number | Adsorbent | DMAC ppm | DMAC removal rate % |
|---|---|---|---|
| 1 | none | 2050 | 0.0 |
| 2 | alumina D25 | 611 | 70.2 |
| 3 | alumina A25 | 502 | 75.5 |
| 4 | silica gel B | 0 | >99.9 |
| 5 | silica gel RD | 0 | >99.9 |

2. Activated alumina (available from Procatalyse Inc., trade name: PSG-D25)
3. Activated alumina (available from Procatalyse Inc., trade name: PSG-A25)
4. Fuji Silysia Chemical Ltd, Silica gel, spherical B-type
5. Fuji Silysia Chemical Ltd, Silica gel, spherical RD-type Example 4

Into a 500-ml separatory funnel of fluoro resin (PFA), 200 g of ion-exchanged water, 200 g of 1,1,1,3,3-pentachloropropane, 0.2 g of iron complex and 0.1 g of N,N-dimethylacetamide (DMAC) were fed. The resulting solution was stirred by vigorous shaking for 5 minutes at room temperature and left still until the solution was separated into two layers. Then, the organic layer was analyzed by gas chromatograph. As a result, no DMAC was detected in the organic layer. No iron content was also detected in the organic layer.

It has been shown by the above results that it is possible to remove the iron complex and DMAC by washing with water.

Example 5

Production of 1-chloro-3,3,3-trifluoropropene

A gas-phase reactor, a cylindrical reaction tube (SUS 316L, diameter: 1 inch, length: 30 cm) with an electric furnace was provided. The reaction tube was packed with 150 cc of the gas-phase fluorination catalyst prepared in Preparation Example 1. While flowing nitrogen gas through the reaction tube at a flow rate of about 320 cc/min, the temperature of the reaction tube was raised to 300° C. Hydrogen fluoride was fed at a rate of about 0.40 g/min together with the nitrogen gas. The temperature of the reaction tube was further raised to a maximum catalyst treatment temperature of 350° C. and maintained for 1 hour. After that, the temperature of the reaction tube was lowered to 250° C. Further, the feeding rate of the hydrogen chloride was set to 0.4 g/min. In this state, the 1,1,1,3,3-pentachloropropane of Test No. 1 of Example 3 was fed in gas form into the reactor at a rate of 1.0 g/min.

After the lapse of 1 hour from the initiation of the reaction, the reaction was stabilized. The product gas flowing out of the reaction tube was blown into water for removal of acid gas components, and then, collected in a dry-ice-acetone trap over 2 hours after the stabilization of the reaction. With this, 65.2 g of the organic substance was obtained. It was confirmed by gas chromatographic analysis of the collected organic substance that: the conversion rate of the 1,1,1,3,3-pentachloropropane was 99.9% or more; and the selectivity of the target 1-chloro-3,3,3-trifluoropropene was 92.4% (trans/cis isomer ratio: about 10/1).

Comparative Example 1

Production of 1-chloro-3,3,3-trifluoropropene

The reaction was subsequently performed by feeding hydrogen fluoride at a rate of about 0.4 g/mm and feeing the 1,1,1,3,3-pentachloropropane of Test No. 4 of Example 3, which contained 1140 ppm of DMAC hydrochloride salt, in gas form into the reactor under the same conditions as in Example 5. The product gas flowing out of the reaction tube was blown into water for removal of acid gas components, and then, collected in a dry-ice-acetone trap over 2 hours after the lapse of 1 hour from the initiation of the reaction. With this, 80.2 g of the organic substance was obtained. It was confirmed by gas chromatographic analysis of the collected organic substance that: the conversion rate of the 1,1,1,3,3-pentachloropropane was 79.3%; and the selectivity of the target 1-chloro-3,3,3-trifluoropropene was 91.3% (trans/cis isomer ratio: about 10/1).

As is apparent from the above results, the catalytic activity of the catalyst was deteriorated rapidly when the 1,1,1,3,3-pentachloropropane containing DMAC hydrochloride salt was used as the raw material.

Example 6

Production of 1,1,1,3,3-pentachloropropane

Into a 1000-ml glass autoclave reactor with a stirrer, 3.2 mol of carbon tetrachloride, 0.8 mol of chloroform, 0.06 mol of N,N-dimethylacetamide (DMAC) (1.25 mol % relative to the carbon tetrachloride) and 0.02 mol of iron powder (0.625 mol % relative to the carbon tetrachloride) were fed. The reactor was sealed after the air inside the reactor was replaced with nitrogen gas. Then, the content of the reactor was heated to 140° C. and maintained for 30 minutes while stirring at 250 rpm. At this time, the pressure of the reactor was 0.25 MPaG (gauge pressure; hereinafter, the same applies to the following). After the lapse of 30 minutes, vinyl chloride was injected into the reactor so that the pressure of the reactor became approximately 0.33 MPaG. With the progress of the reaction, vinyl chloride was further injected into the reactor so as to maintain the pressure of the reactor. The total amount of the vinyl chloride injected was 2 mol. The reaction time was 160 minutes.

After the completion of the reaction, the reactor was cooled naturally. The content was taken out of the reactor and analyzed by gas chromatograph.

The yield of the target 1,1,1,3,3-pentachloropropane relative to the amount of the carbon tetrachloride fed was 55.1 mol %. The amount of the carbon tetrachloride remaining unreacted was 1.35 mol (42.2% relative to the amount of the carbon tetrachloride fed). The reaction rate of the vinyl chloride and the selectivity of the 1,1,1,3,3-pentachloropropane were 97.6% and 92.7%, respectively. Further, the target compound contained 500 ppm of DMAC hydrochloride salt and 1100 ppm of iron complex.

Removal of DMAC Hydrochloride Salt Etc. From 1,1,1,3, 3-Pentachloropropane by Adsorption on Adsorbent The above-obtained 1,1,1,3,3-pentachloropropane, which contained 500 ppm of the DMAC hydrochloride salt and 1100 ppm of the iron complex, was placed together with an adsorbent (activated alumina available from Sumitomo Chemical Co., Ltd.) in a 100-ml glass bottle with a screw cap. The resulting organic substance was left for 30 minutes at room temperature. After that, the organic substance was dried and subjected to distillation purification. It was confirmed by gas chromatographic analysis of the organic substance that the concentration of the iron complex and the concentration of the DMAC hydrochloride salt were reduced to 99 ppm and 90 ppm, respectively.

After the removal of the DMAC hydrochloride salt and iron complex by the above adsorption operation, unreacted carbon tetrachloride and the like were removed by vacuum distillation. The resulting 1,1,1,3,3-pentachloropropane was used as the raw material for the following production of 1-chloro-3, 3,3-trifluoropropene.

Production of 1-chloro-3,3,3-trifluoropropene

A gas-phase reactor, a cylindrical reaction tube (SUS 316L, diameter: 1 inch, length: 30 cm) with an electric furnace was provided. The reaction tube was packed with 150 cc of the gas-phase fluorination catalyst prepared in Preparation Example 1. While flowing nitrogen gas through the reaction tube at a flow rate of about 320 cc/min, the temperature of the reaction tube was raised to 300° C. Then, hydrogen fluoride was fed at a rate of about 0.40 g/min together with the nitrogen gas. The temperature of the reaction tube was further raised to a maximum catalyst treatment temperature of 350° C. and maintained for 1 hour. After that, the temperature of the reaction tube was lowered to 250° C. Further, the feeding rate of the hydrogen chloride was set to 0.4 g/min. The above-obtained 1,1,1,3,3-pentachloropropane, which contained 99 ppm of the iron complex and 90 ppm of the DMAC hydrochloride salt, was then fed in gas form into the reactor at a rate of 1.0 g/min.

After the lapse of 1 hour from the initiation of the reaction, the reaction was stabilized. The product gas flowing out of the reaction tube was blown into water for removal of acid gas components, and then, collected in a dry-ice-acetone trap over 2 hours after the stabilization of the reaction. With this, 65.2 g of the organic substance was obtained. It was confirmed by gas chromatographic analysis of the collected organic substance that: the conversion rate of the 1,1,1,3,3-pentachloropropane was 99.9% or more; and the selectivity of the target 1-chloro-3,3,3-trifluoropropene was 92.4% (trans/cis isomer ratio: about 10/1).

Comparative Example 2

Production of 1,1,1,3,3-pentachloropropane

The production of 1,1,1,3,3-pentachloropropane was conducted using the same feeding amounts and under the same reaction conditions as those of Example 6. The thus-obtained 1,1,1,3,3-pentachloropropane contained 500 ppm of MDAC hydrochloride and 1100 ppm of iron complex. This propene was subjected to removal of unreacted carbon tetrachloride and the like by vacuum distillation and used as it is, without removal of the DMAC hydrochloride etc. by adsorption on an adsorbent or washing with water, as the starting material for the following production of 1-chloro-3,3,3-trifluoropropene.

Production of 1-chloro-3,3,3-trifluoropropene

The reaction was performed by feeding hydrogen chloride at a rate of about 0.4 g/min and feeding the above-obtained 1,1,1,3,3-pentachloropropane, which contained 500 ppm of the MDAC hydrochloride and 1100 ppm of the iron complex, in gas form into the reactor at a rate of 1.0 g/min. The product gas flowing out of the reaction tube was blown into water for removal of acid gas components, and then, collected in a dry-ice-acetone trap over 2 hours after the lapse of 1 hour from the initiation of the reaction. With this, 80.2 g of the organic substance was obtained. It was confirmed by gas chromatographic analysis of the collected organic substance that: the conversion rate of the 1,1,1,3,3-pentachloropropane was 68.5%; and the selectivity of the target 1-chloro-3,3,3-trifluoropropene was 92.1% (trans/cis isomer ratio: about 10/1).

As is apparent from the above results, the catalytic activity of the catalyst was deteriorated rapidly when the 1,1,1,3,3-pentachloropropane containing 500 ppm of the DMAC hydrochloride and 1100 ppm of the iron complex was used as the raw material.

INDUSTRIAL APPLICABILITY

The target compound of the present invention, 1-chloro-3, 3,3-trifluoropropene, is useful as an agrichemical product, pharmaceutical product, coolant, wording fluid, blowing agent, functional material and intermediate for fluorinated hydrocarbons.

The invention claimed is:
1. A method for producing 1-chloro-3,3,3-trifluoropropene, comprising reacting 1,1,1,3,3-pentachloropropane with hydrogen fluoride in a reaction system,
wherein the method comprises a concentration control step of controlling the concentrations of a metal solubilizer and/or a hydrochloride salt thereof and an iron complex in the 1,1,1,3,3-pentachloropropane supplied to the reaction system to be 100 ppm or less.
2. The method according to claim 1, wherein the metal solubilizer is at least one selected from the group consisting of N,N-dimethylacetamide, acetonitrile, 2-aminoacetonitrile, N,N-dimethylformamide and hexamethylphosphoric amide.
3. The method according to claim 1, wherein the iron complex is a complex of N,N-dimethylacetamide, iron (II) chloride and iron (III) chloride ($FeCl_2 \cdot 2FeCl_3 \cdot 6DMAC$).
4. The method according to claim 1, wherein the concentration control step includes, before supplying the 1,1,1,3,3-pentachloropropane to the reaction system, removing the metal solubilizer and/or the hydrochloride salt thereof and the iron complex from the 1,1,1,3,3-pentachloropropane by adsorption onto an adsorbent.

5. The method according to claim 1, wherein the concentration control step includes, before supplying the 1,1,1,3,3-pentachloropropane to the reaction system, removing the metal solubilizer and/or the hydrochloride salt thereof and the iron complex from the 1,1,1,3,3-pentachloropropane by washing with water.

6. The method according to claim 1, further comprising: forming the 1,1,1,3,3-pentachloropropane by reaction of carbon tetrachloride and vinyl chloride in the presence of an iron catalyst.

7. The method according to claim 6, wherein the concentration of the iron catalyst used in the reaction of the carbon tetrachloride and the vinyl chloride is 100 ppm or less in terms of iron.

8. The method according to claim 1, wherein the 1,1,1,3,3-pentachloropropane is reacted with the hydrogen fluoride in the absence of a catalyst in a temperature range of 100 to 500° C. and in a pressure range of 0.05 to 6.0 MPa.

9. The method according to claim 1, wherein the 1,1,1,3,3-pentachloropropane is reacted with the hydrogen fluoride in a gas phase in the presence of a fluorination catalyst.

10. The method according to claim 9, wherein the fluorination catalyst is at least one selected from the group consisting of fluorinated stainless steel, fluorinated alumina, fluorinated zirconia, fluorinated titania, activated carbon, chromium-carried alumina and chromium-carried activated carbon.

* * * * *